US008809005B2

(12) United States Patent
Stubenrauch et al.

(10) Patent No.: US 8,809,005 B2
(45) Date of Patent: Aug. 19, 2014

(54) CONJUGATE AND ITS USE AS A STANDARD IN AN IMMUNOASSAY

(75) Inventors: Kay-Gunnar Stubenrauch, Penzberg (DE); Rudolf Vogel, Weilheim (DE); Uwe Wessels, Penzberg (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 166 days.

(21) Appl. No.: 11/941,116

(22) Filed: Nov. 16, 2007

(65) Prior Publication Data
US 2008/0118939 A1 May 22, 2008

(30) Foreign Application Priority Data
Nov. 21, 2006 (EP) ..................................... 06024133

(51) Int. Cl.
| C07K 16/42 | (2006.01) |
| G01N 33/543 | (2006.01) |
| G01N 33/553 | (2006.01) |
| G01N 33/563 | (2006.01) |
| G01N 33/68 | (2006.01) |
| C07K 16/46 | (2006.01) |
| C12P 21/08 | (2006.01) |
| G01N 21/59 | (2006.01) |

(52) U.S. Cl.
CPC .......... G01N 33/686 (2013.01); C07K 16/4208 (2013.01); C07K 16/4283 (2013.01); C07K 16/4291 (2013.01); C07K 16/461 (2013.01); G01N 33/543 (2013.01); G01N 33/553 (2013.01); G01N 33/6857 (2013.01); *G01N 2021/5903* (2013.01); *G01N 2333/435* (2013.01); *G01N 2800/24* (2013.01); *G01N 2800/52* (2013.01); *C07K 2316/52* (2013.01); *C07K 2317/24* (2013.01); *C07K 2317/54* (2013.01)
USPC .......... 435/7.94; 436/512; 436/513; 436/518; 436/524; 436/527; 530/387.2; 530/391.1; 530/391.3; 530/402

(58) Field of Classification Search
CPC .............. G01N 33/543; G01N 33/553; G01N 33/6857; G01N 33/686; G01N 2021/5903; G01N 2333/435; G01N 2800/24; G01N 2800/52; C07K 16/4208; C07K 16/4283; C07K 16/4291; C07K 16/461; C07K 2316/52; C07K 2317/24; C07K 2317/54; C07K 2317/55; C07K 2317/64
USPC ......... 435/7.94; 436/512, 513, 518, 524, 527; 530/391.1, 391.3, 387.2, 402
See application file for complete search history.

(56) References Cited

U.S. PATENT DOCUMENTS

| 4,513,088 | A | * | 4/1985 | Levy et al. .................... 435/7.23 |
| 4,661,444 | A | | 4/1987 | Li |
| 5,780,029 | A | | 7/1998 | Ferrone |
| 5,977,315 | A | * | 11/1999 | Chatterjee et al. ......... 530/387.2 |
| 6,063,379 | A | * | 5/2000 | Vazguez Lopez et al. . 424/130.1 |
| 2003/0118593 | A1 | | 6/2003 | Dan et al. |
| 2004/0253233 | A1 | * | 12/2004 | Del Rio et al. ............. 424/142.1 |
| 2005/0222392 | A1 | | 10/2005 | Carter et al. |

FOREIGN PATENT DOCUMENTS

| EP | 0113431 | 7/1984 |
| EP | 0 139 389 | 5/1985 |
| EP | 0 170 302 | 2/1986 |
| EP | 0488277 | 6/1992 |
| EP | 0508282 | 10/1992 |
| JP | 60-248626 | 12/1985 |
| WO | WO 87/02778 | 5/1987 |
| WO | 90/04413 | 5/1990 |
| WO | 97/23237 | 7/1997 |
| WO | WO 99/02545 | 1/1999 |
| WO | 02/081496 | 10/2002 |
| WO | WO 03/084996 | 10/2003 |
| WO | 2005/019271 | 3/2005 |
| WO | WO 2005/045058 A2 | 5/2005 |
| WO | WO 2005/045058 A3 | 5/2005 |
| WO | WO 2005/077981 | 8/2005 |

OTHER PUBLICATIONS

Hastings et al., 1992. Production and characterization of a murine/human chimeric anti-idiotype antibody that mimics ganglioside. Cancer Research 52: 1681-1686.*

McLaughlin et al., 1998. Rituximab chimeric anti-CD20 monoclonal antibody therapy for relapsed indolent lymphoma: half of patients respond to a four-dose treatment program. Journal of Clinical Oncology 16: 2825-2833.*

Hamblin et al., 1987. Initial experience in treating human lymphoma with a chimeric univalent derivative of monclonaql anti-idiotypic antibody. Blood 69: 790-797.*

Knight et al., 1995. The immunogenicity of the 7E3 murine monoclonal Fab antibody fragment variable region is dramatically reduced in humans by substitution of human for murine constant regions. Mol. Immunol. 32: 1271-1281.*

Kwak et al., 1992. induction of immune responses in patients with B-cell lymphoma against the surface-immunoglobulin idiotype expressed by their tumors. New England J. Medicine 327: 1209-1215.*

(Continued)

Primary Examiner — Mark Shibuya
Assistant Examiner — James L Grun

(57) ABSTRACT

A composition comprising a conjugate of an anti-idiotype antibody specifically binding to a CDR region of a parent antibody and method of using polyclonal human serum immunoglobulin of class E, G, M, or A, and the use of said composition as a standard in an immunoassay is presented.

8 Claims, 7 Drawing Sheets

(56) References Cited

OTHER PUBLICATIONS

Figure 1:
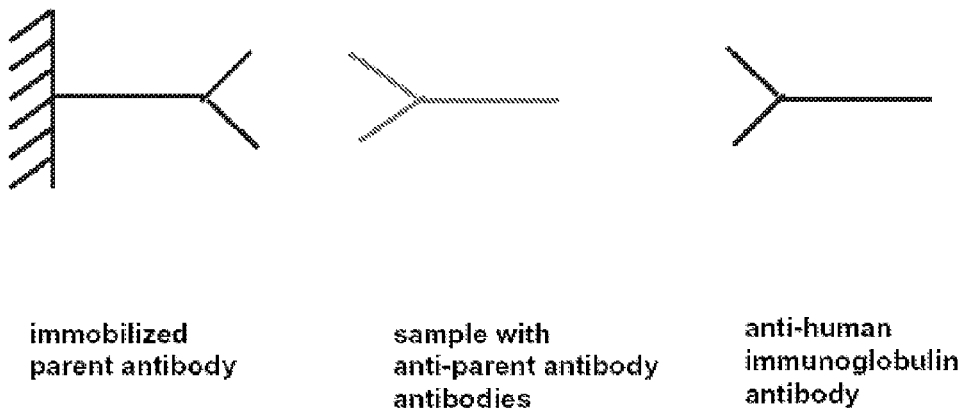

Shankar et al., Jun. 2006. Scientific and regulatory considerations on the immunogenicity of biologics. Trends in Biotechnol. 24: 274-280.*

Stevenson et al., 1984. Chimeric univalent antibodies for treating lymphoid malignancies. Med. Oncol. Tumor Pharmacother. 1: 275-278.*

Solomon G et al, *Proceedings of the Nat'l Acad. of Sciences of USA*, 80(3) (1983) 850-854 XP002430126.

Translation of Korean Office Action in Corresponding Serial No. 2009-7010812.

Taiwanese Office Action with Translated Search Report dated Feb. 10, 2011.

The English translation of the Japanese Decision to Grant a Patent, issued on Mar. 13, 2013, in the corresponding Japanese application No. 2009-537520., pp. 3 (Mar. 13, 2013).

(Translation of Japanese Office Act. for Corres. Case 2009-537520 Jun. 22, 2011).

Hoesel, W., *J. Immunol Methods*, 294 (2004) 101-110.

Mire-Sluis, A.R. et al, *J. Immunol. Methods*, 289 (2004) 1-16.

Wadhwa, M. et al, *J. Immunol. Methods*, 278 92003) 1-17.

Ritter, G. *Cancer Res.* 61 (2001) 6851-6859.

Butler, J.E., *Immunoassays*, (1996) p. 205-225.

Levene, A.P. et al, *Jour. of the Royal Soc. of Med.*, 98 (2005) 146-152.

Pink, J.R. et al, *Biochem, J.*, 117 (1970) 33-47.

Pan, Y. et al, *FASEB J.*, 9 (1995) 43-49.

Mihara, M. et al, *Clin. Immunol*, 98 (2001) 319-326.

Nishimoto, N et al, *Blood* 106 (2005) 2627-2632.

Lu, B. et al, *Analyst* 121 (1996) 29R-32R.

Wilchek, M. et al, *Methods Enzymol*, 184 (1990) 467-469.

Martin, C.R. et al, *Anal. Chem—News & Features* 70 (1998) 322A-327A.

* cited by examiner

CONJUGATE AND ITS USE AS A STANDARD IN AN IMMUNOASSAY

PRIORITY TO RELATED APPLICATION(S)

This application claims the benefit of European Patent Application No. 06024133.8, filed Nov. 21, 2006, which is hereby incorporated by reference in its entirety.

FIELD OF THE INVENTION

The invention comprises a conjugate and its use as a standard or positive control in an immunoassay for the determination of anti-drug antibodies.

BACKGROUND OF THE INVENTION

Standard solid-phase immunoassays with monoclonal antibodies involve the formation of a complex between an antibody adsorbed on a solid support (capture antibody), the antigen, and an antibody to another epitope of the antigen conjugated with a detectable label (tracer antibody). Thus, a sandwich is formed: solid support-capture antibody-antigen-tracer antibody. In the sandwich, the intensity of the antibody-conjugated detectable label is proportional to the antigen concentration in the incubation medium. The standard sandwich method is also called double antigen bridging immunoassay because capture and tracer antibodies bind to different epitopes of the antigen. Hoesel, W., et al., in J. Immunol. Methods 294 (2004) 101-110, report an anti-EPO double antigen bridging assay whereby a mixture of immobilized rhEPO coupled to amino groups and to carbohydrate groups was used.

Immunoassays such as the double antigen bridging ELISA are common assay types in the investigation of an immunogenic answer of a patient to an antibody drug (therapeutic or diagnostic antibody). Mire-Sluis, A. R., et al., in J. Immunol. Methods 289 (2004) 1-16, summarize the recommendations for the design and optimization of immunoassays using detection of host antibodies against biotechnology products. According to Mire-Sluis et al. the well-known anti-drug antibody assay formats show considerable disadvantages. Anti-drug antibody assays are mentioned, for example, in WO 2005/045058; and WO 90/006515. Anti-idiotypic antibody assays are mentioned, for example, in U.S. Pat. No. 5,219,730; WO 87/002778; EP 0 139 389; and EP 0 170 302. Wadhwa, M., et al., in J. Immunol. Methods 278 (2003) 1-17, report strategies for the detection, measurement and characterization of unwanted antibodies induced by therapeutic biologicals.

Serological analysis of human anti-human antibodies is described in Ritter, G., Cancer Res. 61 (2001) 6851-6859, and WO 2003/016909. The identification of human anti-human antibodies of IgG class requires an additional step of protein G precipitation prior to the assay.

SUMMARY OF THE INVENTION

The invention comprises a conjugate comprising an anti-idiotype antibody specifically binding to a CDR region of a parent antibody and a reference immunoglobulin of a single immunoglobulin class, and preferably wherein said reference immunoglobulin is not specifically binding said anti-idiotype antibody and said parent antibody.

The invention further comprises a method in an immunoassay for the determination of an anti-parent-antibody antibody in a sample of a human being, using a sandwich immunoassay comprising a capture antibody and a tracer antibody, and use of the conjugate of the invention as a standard or positive control.

The invention further comprises a method for the determination of the immunoglobulin class of an anti-idiotype antibody specifically binding a CDR region of a parent antibody in a sample using a sandwich immunoassay comprising a capture antibody and a tracer antibody and a conjugate comprising an anti-idiotype antibody specifically binding to a CDR region of a parent antibody and a reference immunoglobulin of a single immunoglobulin class, comprising the following steps:
a) contacting said sample with the capture antibody under conditions suitable for the formation of a capture antibody/anti-idiotype antibody-complex,
b) contacting separately
  i) an anti-human-immunoglobulin-A antibody,
  ii) an anti-human-immunoglobulin-E antibody,
  iii) an anti-human-immunoglobulin-M antibody, and
  iv) an anti-human-immunoglobulin-G antibody
as tracer antibodies with said capture antibody/anti-idiotype antibody-complex,
c) determining the binding of said tracer antibodies to said complex and thereby determining the immunoglobulin class of said anti-idiotype antibody,
wherein said conjugate is used as a positive control.

DETAILED DESCRIPTION OF THE FIGURES

FIG. 1 Scheme for the detection of anti-parent-antibody antibodies in a sample with optional subsequent subclass determination.

Figure 2:
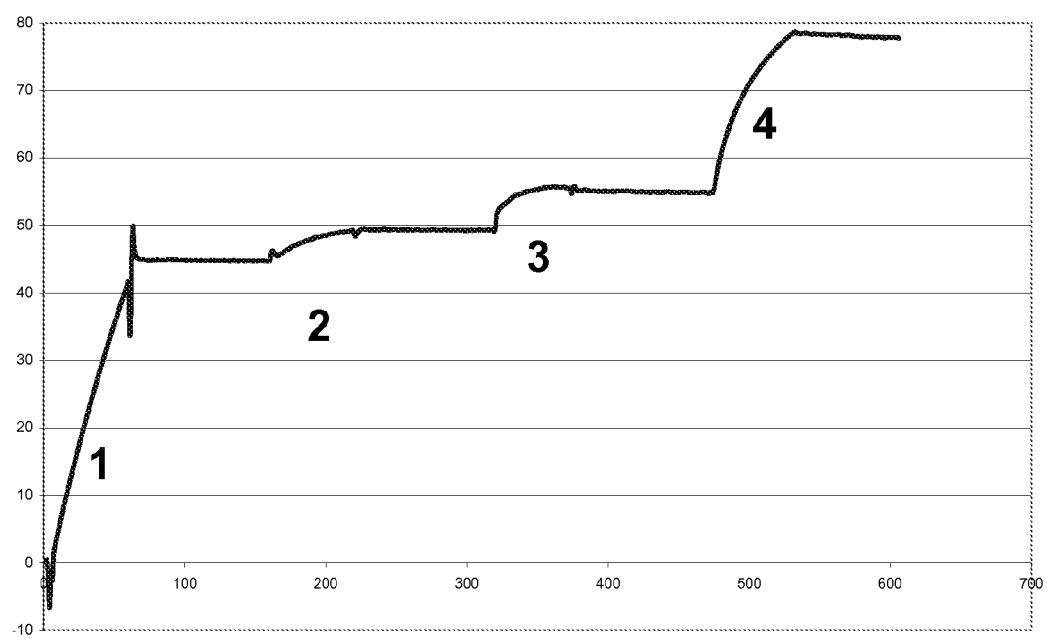

FIG. 2 BIAcore SPR diagram for the subclass determination of an anti-idiotype antibody according to the invention. (1) Injection of sample, (2)+(3) injection of anti-human-immunoglobulin-E antibody, (4) injection of anti-human-immunoglobulin-G antibody.

Figure 3:
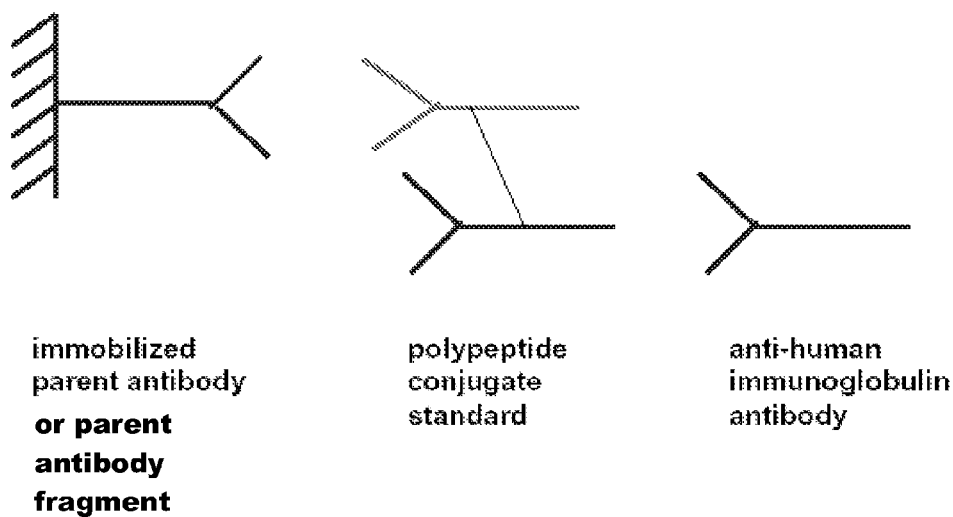

FIG. 3 Scheme for the use of a conjugate according to the invention as a standard with an optional class specific antibody.

Figure 4:
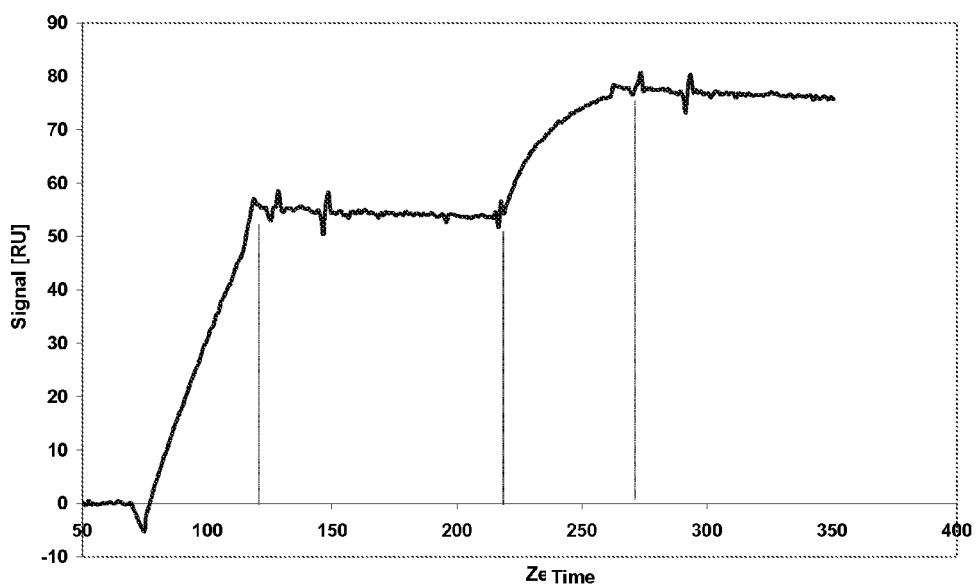

FIG. 4 BIAcore SPR diagram for the use of a compound according to the invention as standard (first response) with an optional subsequent anti-standard immunoglobulin subclass antibody (second response).

Figure 5:
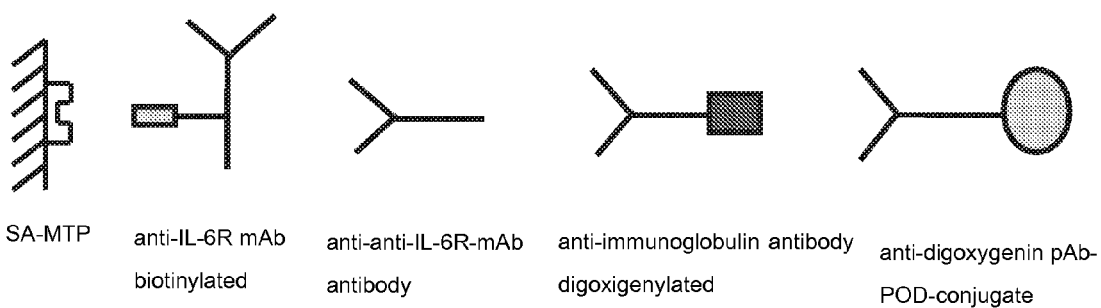

FIG. 5 Scheme of an ELISA-determination of an anti-idiotypic antibody.

Figure 6:
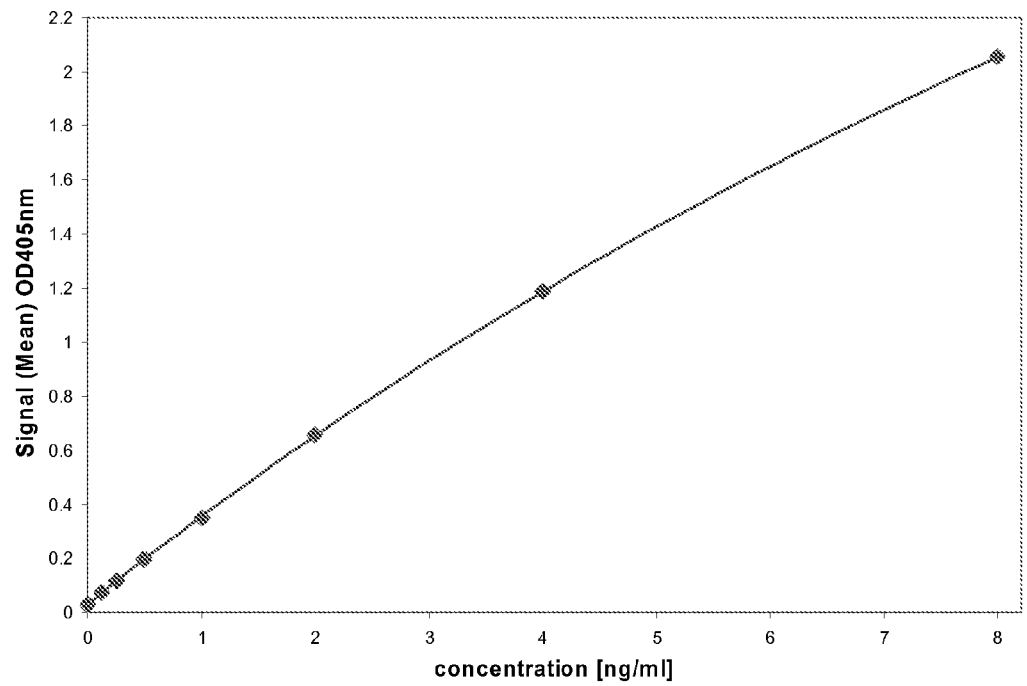

FIG. 6 Standard curve of an ELISA for the determination of anti-idiotypic antibody.

Figure 7:
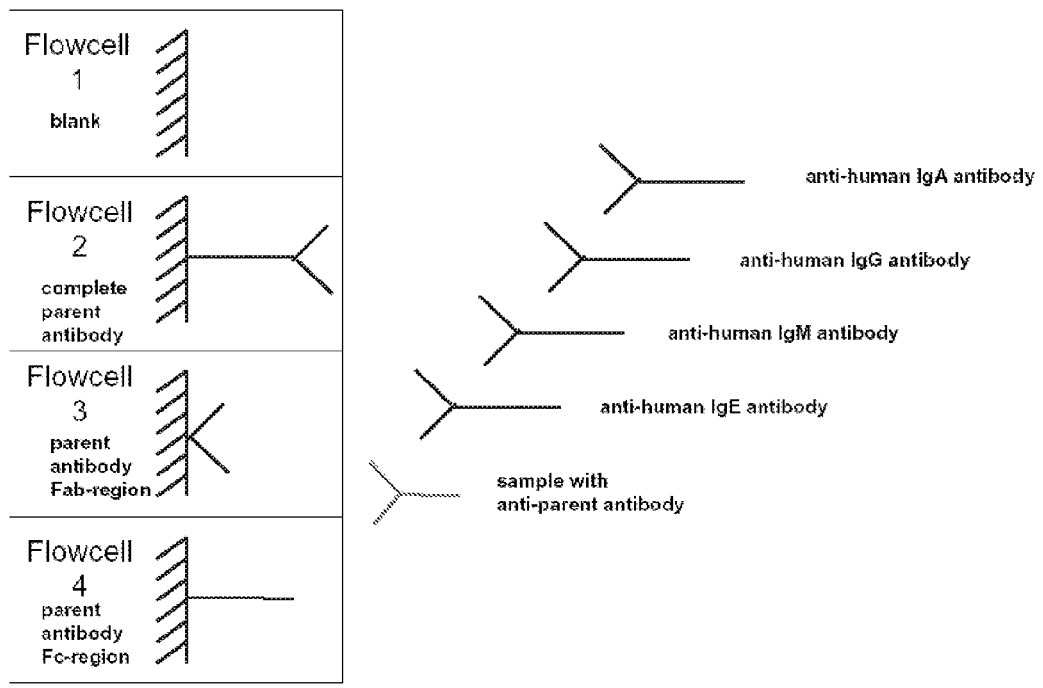

FIG. 7 Scheme of a multiple channel detection of the binding region of an anti-parent-antibody antibody with subsequent immunoglobulin class determination.

DETAILED DESCRIPTION OF THE INVENTION

The current invention generally comprises a conjugate comprising an anti-idiotype antibody specifically binding to a CDR region of a parent antibody and a reference immunoglobulin of a single immunoglobulin class.

The invention further comprises a conjugate comprising an anti-idiotype antibody specifically binding to a CDR region of a parent antibody and a reference immunoglobulin of a single immunoglobulin class, and preferably wherein said reference immunoglobulin is not specifically binding said anti-idiotype antibody and said parent antibody.

Preferably said capture antibody or said tracer antibody is said parent antibody.

Preferably said anti-parent-antibody antibody is an anti-idiotype antibody against said parent antibody.

Preferably said parent antibody is a therapeutic antibody or a diagnostic antibody.

The invention further comprises a method in an immunoassay for the determination of an anti-parent-antibody antibody in a sample of a human being, using a sandwich immunoassay comprising a capture antibody and a tracer antibody.

The invention further comprises a method for the determination of the immunoglobulin class of an anti-idiotype antibody specifically binding a CDR region of a parent antibody in a sample using a sandwich immunoassay comprising a capture antibody and a tracer antibody and the conjugate of claim 1, comprising the following steps:
a) contacting said sample with the capture antibody under conditions suitable for the formation of a capture antibody/anti-idiotype antibody-complex,
b) contacting separately
   i) an anti-human-immunoglobulin-A antibody,
   ii) an anti-human-immunoglobulin-E antibody,
   iii) an anti-human-immunoglobulin-M antibody, and
   iv) an anti-human-immunoglobulin-G antibody
as tracer antibodies with said capture antibody/anti-idiotype antibody-complex,
c) determining the binding of said tracer antibodies to said complex and thereby determining the immunoglobulin class of said anti-idiotype antibody,
wherein the conjugate of claim 1 is used as a positive control.

Preferably the capture antibody is selected from the group comprising the light chain, the variable region of the heavy chain, a Fab, Fab', F(ab)$_2$, or F(ab')$_2$ fragment of said parent antibody.

Preferably conjugation of the capture antibody to the solid support is performed by passive adsorption.

Preferably the capture antibody is immobilized via a specific binding pair.

Preferably the capture antibody is conjugated to biotin and immobilization is performed via immobilized Avidin or Streptavidin.

Preferably the tracer antibody is conjugated to a detectable label via a specific binding pair.

Preferably the tracer antibody is conjugated to digoxigenin and linking to the detectable label is performed via an antibody against digoxigenin.

Preferably the immunological determination is performed by surface plasmon resonance.

Preferably conjugation of the capture and/or tracer antibody to its conjugation partner is performed by chemically binding it via N-terminal and/or ε-amino groups (lysine), ε-amino groups of different lysines, carboxy-, sulfhydryl-, hydroxyl-, and/or phenolic functional groups of the amino acid backbone of the antibody, and/or sugar alcohol groups of the carbohydrate structure of the antibody.

Preferably the capture antibody is conjugated to the solid support by passive adsorption and therefore the capture antibody conjugated to the solid support comprises a mixture of at least two capture antibodies which are conjugated to the solid support via different antibody sites. Passive adsorption is, e.g., described by Butler, J. E., Solid Phases in Immunoassay, In: Immunoassays, Diamandis, E. P. and Christopoulos, T. K. (eds.), Academic Press San Diego (1996), pp. 205-225 (hereby incorporated by reference).

In a preferred embodiment of the invention, the capture antibody is immobilized via a specific binding pair. Such a binding pair (first component/second component) is, for example, Streptavidin or Avidin/biotin, antibody/antigen (see, for example, Hermanson, G. T., et al., Bioconjugate Techniques, Academic Press, 1996), lectin/polysaccharide, steroid/steroid binding protein, hormone/hormone receptor, enzyme/substrate, IgG/Protein A and/or G, etc. Preferably, the capture parent antibody is conjugated to biotin and immobilization is performed via immobilized Avidin or Streptavidin.

In a preferred embodiment of the invention, the tracer antibody is conjugated to a detectable label, preferably conjugated via a specific binding pair. Such a binding pair (first component/second component) is, for example, Streptavidin or Avidin/biotin, antibody/antigen (see, for example, Hermanson, G. T., et al., Bioconjugate Techniques, Academic Press, 1996), lectin/polysaccharide, steroid/steroid binding protein, hormone/hormone receptor, enzyme/substrate, IgG/Protein A and/or G, etc. Preferably, the tracer parent antibody is conjugated via digoxigenin and an antibody against digoxigenin to the detectable label. Alternatively the tracer parent antibody is conjugated to an electrochemiluminescent label, like a ruthenium bispyridyl complex.

Definitions

The term "anti-idiotype antibody specifically binding to a CDR region of a parent antibody" according to the invention denotes an antibody rose against a parent antibody in a non-human animal, i.e. a non-human antibody. Preferably said antibody raised against a parent antibody is raised in a rodent or a macaque, especially preferred in a mouse, a rabbit, or a cynomolgus, or obtained by a display technique, preferably by phage- or ribosome-display. Preferably the anti-idiotype antibody is a polyclonal antibody. Also preferably the anti-idiotype antibody is a monoclonal antibody. Immunization of the animal is performed preferably with the parent antibody or fragments thereof. In a further step, immunoglobulin from said animal is isolated and purified using affinity adsorption to a/the CDR region(s) of the parent antibody. The term "CDR region of a parent antibody" denotes the CDR regions of the parent antibody's light and heavy chain, i.e. comprises the parent antibody light chain CDR1, CDR2, CDR3, the parent antibody heavy chain CDR1, CDR2, CDR3.

The term "parent antibody" according to the invention denotes an antibody which can be administered as a drug (drug antibody or therapeutic antibody) or as a diagnostic means (diagnostic antibody) to an individual, so that a sample of said individual is suspected to comprise said parent antibody after administration. Within one assay performed according to the invention the parent antibody, the capture (parent) antibody, and/or the tracer (parent) antibody comprise the "same" antibody molecule, e.g. recombinantly produced with the same expression vector and comprising the same amino acid sequence. Drug antibodies (therapeutic monoclonal antibodies) are being used widely for the treatment of various diseases such as oncological diseases (e.g. hematological and solid malignancies including non-Hodgkin's lymphoma, breast cancer, and colorectal cancer). Such antibodies are described, for example, by Levene, A. P., et al., Journal of the Royal Society of Medicine 98 (2005) 146-152. Such antibodies are, for instance, antibodies against CCR4, CD19, CD20, CD22, CD28, HLA-DR, CD33, CD40, CD52, CD80, CSF-1R, CTLA-4, fibroblast activation protein (FAP), EGFR, G250, GD3, HER2/neu, HER3, HER4, prostate-specific membrane antigen (PSMA), CD56, VEGF, VEGF2, TLSP-R, TIE-1, TIE-2, TNF-alpha, TNF like weak inducer of apoptosis (TWEAK), CEA, Ep-CAM, TRAIL, TRAIL-receptor 1, TRAIL-receptor 2, lymphotoxin-beta receptor, Levis Y antigen, hepsin, melanoma-associated chondroitin sulfate proteoglycan (MCSP), IL-1 receptor, IL-6 receptor, VEGF-receptor 1, VEGF-receptor 2, or IGF-1 receptor. Therapeutic antibodies are also described by Groner, B., et al., Curr. Mol. Med. 4 (2004) 539-547, and Harris, M., Lancet Oncol. 5 (2004) 292-302.

The term "reference immunoglobulin" as used herein denotes a complete immunoglobulin, i.e. an immunoglobulin comprising a Fab region and an Fc region, as well as fragments of a complete immunoglobulin, such as the Fc-region, the $C_H2$ domain, or the $C_H3$ domain. The reference immunoglobulin is preferably a human immunoglobulin. Preferably the "reference immunoglobulin" is a human immunoglobulin or an $F_C$-region of a human immunoglobulin. The "reference immunoglobulin" is not specifically binding the anti-idiotype antibody and not specifically binding the parent antibody of the conjugate according to the invention. The Fc-region of an immunoglobulin is obtained by pepsin or papain cleavage of a complete immunoglobulin. The reference immunoglobulin is of a "single immunoglobulin class". The term "single immunoglobulin class" denotes that the reference immunoglobulin comprises an immunoglobulin class specific constant region amino acid sequence selected from the immunoglobulin classes A, E, M, and G. For immunoglobulin class specific constant region amino acid sequences see e.g. Pink, J. R., et al., Biochem. J. 117 (1970) 33-47.

An "anti-parent-antibody antibody" is an antibody specifically binding the parent antibody, i.e. an antibody against a parent antibody. Likewise is an anti-anti-IL-6R-antibody antibody an antibody specifically binding an anti-IL-6R antibody. An "anti-parent-antibody antibody" is an antibody directed against any region of the parent antibody, like the variable region, the constant region or the glycostructure of the parent antibody. Such anti-parent-antibody antibodies may occur during antibody therapy as an immunogenic reaction of a patient (see Pan, Y., et al., FASEB J. 9 (1995) 43-49). An "anti-idiotype antibody" is an antibody specifically binding to a CDR region of a parent antibody. An anti-idiotype antibody specifically binds to the light chain CDR1 region, the light chain CDR2 region, the light chain CDR3 region, the heavy chain CDR1 region, the heavy chain CDR2 region, or the heavy chain CDR3 region of a parent antibody.

An example (preferably monoclonal) parent antibody is an antibody against the IL-6 receptor (anti-IL-6R antibody). Such an antibody is for example described by Mihara, M., et al., Clin. Immunol. 98 (2001) 319-326, Nishimoto, N., et al., Blood 106 (2005) 2627-2632, in clinical trial NCT00046774, or in WO 2004/096274.

An example (preferably monoclonal) parent antibody is an antibody against IGF-1 receptor (anti-IGF-1R antibody). Such an antibody is for example described in WO 2004/087756, or in WO 2005/005635.

The term "binding" or "specifically binding" according to the invention refers to binding an antigen, a constant region of an immunoglobulin, a parent antibody, or a CDR region of a parent antibody with a $K_D$ value of less than $10^{-6}$ M (M=mol/l) (e.g. $10^{-12}$ M), more preferably by a $K_D$ value in the range of from $10^{-9}$ M to $10^{-13}$ M in a BIAcore assay. "Non-specific binding" is found if the $K_D$ value is larger than $10^{-5}$ M (e.g. $10^{-4}$ M).

The principles of different immunoassays are described, for example, by Hage, D. S., in Anal. Chem. 71 (1999) 294R-304R. Lu, B., et al., in Analyst 121 (1996) 29R-32R, report the orientated immobilization of antibodies for the use in immunoassays. Avidin-biotin-mediated immunoassays are reported, for example, by Wilchek, M. and Bayer, E. A., in Methods Enzymol. 184 (1990) 467-469.

Antibodies, especially their constant domains, contain amino acid side chain functionalities, i.e. chemical reactive groups, for coupling to a binding partner like a surface, a protein, a polymer (such as PEG, Cellulose, or Polystyrol), an enzyme, or a member of a binding pair. Chemical reactive groups of antibodies are, for example, amino groups (epsilon amino groups of lysines, alpha-amino groups), thiol groups (cystines, cysteines, and methionines), carboxylic acid groups (aspartic acids, glutamic acids), and sugar-alcoholic groups. Such methods are e.g. described by Aslam, M. and Dent, A., Bioconjugation, MacMillan Ref. Ltd. (1999) 50-100.

For conjugation of polypeptides, e.g. to solid supports, suitable chemical protecting agents are required. These form e.g. bonds at unprotected side chain amines and are less stable than and different from those bonds at the N-terminus. Many such chemical protecting agents are known (see for example EP 0 651 761). Preferred chemical protecting agents include cyclic dicarboxylic acid anhydrides like maleic or citraconylic anhydrides.

The term "sample" includes, but is not limited to, any quantity of a substance from a human being. Such substances include, but are not limited to, whole blood, serum, or plasma from an individual, which are the most widely used sources of sample in clinical routine.

Solid supports for immunoassays according to the invention are widely described in the state of the art (see, e.g., Butler, J. E., Methods 22 (2000) 4-23).

The term "solid support" denotes a non-fluid substance, and includes chips, vessels, and particles (including microparticles and beads) made from materials such as polymer, metal (paramagnetic, ferromagnetic particles), glass, and ceramic; gel substances such as silica, alumina, and polymer gels; capillaries, which may be made of polymer, metal, glass, and/or ceramic; zeolites and other porous substances; electrodes; microtiter plates; solid strips; and cuvettes, tubes or other spectrometer sample containers. A solid support component of an assay is distinguished from inert solid surfaces with which the assay may be in contact in that a "solid support" contains at least one moiety on its surface, which is intended to interact with the capture antibody, either directly or indirectly. A solid support may be a stationary component, such as a tube, strip, cuvette, or microtiter plate, or may be non-stationary components, such as beads and microparticles. Microparticles can also be used as a solid support for homogeneous assay formats. A variety of microparticles that allow both non-covalent or covalent attachment of proteins and other substances may be used. Such particles include polymer particles such as polystyrene and poly(methylmethacrylate); gold particles such as gold nanoparticles and gold colloids; and ceramic particles such as silica, glass, and metal oxide particles. See for example Martin, C. R., et al., Analytical Chemistry-News & Features 70 (1998) 322A-327A, which is incorporated herein by reference.

A "chip" is a solid, non porous material, such as metal, glass or plastics. The material may optionally be coated, entirely or in certain areas. On the surface of the material any array of spots is present, either visible or in coordinates. On each spot a defined polypeptide, with or without linker or spacer to the surface of the material, may be immobilized.

All documents mentioned herein, both supra and infra, are hereby incorporated herein by reference.

Chromogens (fluorescent or luminescent groups and dyes), enzymes, NMR-active groups or metal particles, haptens (e.g. digoxigenin), are examples of detectable labels. The detectable label can also be a photoactivatable crosslinking group, e.g. an azido or an azirine group. Metal chelates which can be detected by electrochemoluminescence are also preferred signal-emitting groups used as detectable labels, with particular preference being given to ruthenium chelates, such as e.g. a ruthenium (bispyridyl)$_3^{2+}$ chelate. Suitable ruthenium labeling groups are described, for example, in EP 0 580 979, WO 90/05301, WO 90/11511, and WO 92/14138.

The invention comprises a conjugate comprising an anti-idiotype antibody specifically binding to a CDR region of a parent antibody and a reference immunoglobulin of a single immunoglobulin class.

The invention comprises a conjugate comprising an anti-idiotype antibody specifically binding to a CDR region of a parent antibody and a reference immunoglobulin of a single immunoglobulin class selected from the group comprising human immunoglobulin E, human immunoglobulin G, human immunoglobulin M, or human immunoglobulin A, i.e. the reference immunoglobulin is either of human IgE class, or of human IgG class, or of human IgM class, or of human IgA class.

Preferably the current invention comprises a conjugate comprising an anti-idiotype antibody specifically binding to a CDR region of a parent antibody and a reference immunoglobulin of a single immunoglobulin class not specifically binding said anti-idiotype antibody and not specifically binding said parent antibody.

Preferably said parent antibody is a therapeutic antibody or a diagnostic antibody. Preferably said reference immunoglobulin is a not functionable immunoglobulin of a single immunoglobulin class or an Fc-region of an immunoglobulin of a single immunoglobulin class.

The term "diagnostic antibody" denotes an antibody which is either a natural antibody or a recombinantly produced antibody and which is used for the detection and visualization of its target antigen. A diagnostic antibody is used e.g. in assay systems (e.g. ELISA), or for in vitro imaging. A diagnostic antibody may e.g. be a labeled therapeutic antibody.

Preferably said reference immunoglobulin is a human immunoglobulin or a human immunoglobulin Fc-region.

The reference immunoglobulin provides an immunoglobulin class specific constant region that can be specifically bound by an anti-immunoglobulin-class antibody, such as an anti-human-immunoglobulin-G antibody. Thus the reference immunoglobulin provides the conjugate according to the invention with an immunoglobulin class specific tag, which can be specifically identified by a tag specific antibody. For example, if the tag is an immunoglobulin G constant region a tag specific antibody is an anti-immunoglobulin-G antibody.

Preferably said anti-idiotype antibody is a polyclonal antibody and said reference immunoglobulin is a polyclonal immunoglobulin. Also preferably said anti-idiotype antibody is a polyclonal antibody and said reference immunoglobulin is a monoclonal immunoglobulin. Still preferably said anti-idiotype antibody is a monoclonal antibody and said reference immunoglobulin is a monoclonal immunoglobulin.

The conjugate according to the invention is obtained by chemical conjugation of an anti-idiotype antibody and a reference immunoglobulin.

In the conjugate according to the invention is the anti-idiotype antibody a functionable immunoglobulin and the reference immunoglobulin a not functionable immunoglobulin. This denotes that the anti-idiotype antibody is specifically binding to its target antibody, whereas the reference antibody is not specifically binding any human antigen. The reference antibody is provided in order to present an Fc-region as similar as possible to naturally occurring immunoglobulins and not to bind an antigen. It is also within the scope of the current invention that the anti-idiotype antibody and the reference antibody are not the same antibody, i.e. they differ by at least 20% of the amino acid residues, i.e. they have an identity based on the amino acid sequence of 80% or less. The reference antibody may be a polyclonal antibody or a monoclonal antibody. The term "monoclonal" as used within the current application denotes a population of antibodies produced by a single cell and/or its progeny. The term denotes that the antibodies have the same amino acid sequence, i.e. the antibodies have the identical amino acid sequence despite inadvertent mutations occurring during the propagation of the cell(s) producing it.

The term "not functionable immunoglobulin" as used within this application denotes an immunoglobulin that binds to a human antigen with a $K_D$-value (binding affinity) of $10^{-5}$ mol/l or higher (e.g. $10^{-3}$ mol/l), preferably with a $K_D$-value of $10^{-6}$ mol/l or higher. The binding affinity is determined with a standard binding assay, such as surface plasmon resonance technique (BIAcore®). This binding affinity value has not to be treated as an exact value; it is merely a point of reference. It is used to determine and/or select immunoglobulins that show no immunoglobulin-typical specific binding for human antigens and thus have no therapeutic activity in humans. This does not exclude that the immunoglobulin shows a specific binding for non-human antigens. This specific binding of a non-human antigen is associated with a $K_D$-value of $10^{-7}$ mol/l or lower (e.g. $10^{-10}$ mol/l), preferably with a $K_D$-value of $10^{-8}$ mol/l or lower.

Based on transfectomas, i.e. on lymphoid cells containing transfected immunoglobulin genes obtained from immunized mice, a conjugate according to the invention can be obtained by conjugation on the nucleic acid level.

The administration of drugs to mammals originating from outside the receiving organism, e.g. the administration of exogenous therapeutic polypeptides, results in an immune response of the receiving mammal. This immune response becomes apparent by the occurrence of anti-drug antibodies. For the evaluation of such an immune response a method for the detection of the antibodies against the drug is required.

The conjugate according to the invention can be used as standard in an immunoassay. Thus, the invention comprises the use of a conjugate comprising an anti-idiotype antibody specifically binding to a CDR region of a parent antibody and a reference immunoglobulin of a single immunoglobulin class as a standard in an immunoassay for the determination of an anti-parent-antibody antibody in a sample of a human being.

Also can the conjugate according to the invention be used as a positive control in an immunoassay. It enables e.g. the establishment of a detection limit. Thus, the invention comprises the use of a conjugate comprising an anti-idiotype antibody specifically binding to a CDR region of a parent antibody and a reference immunoglobulin of a single immunoglobulin class as a positive control in an immunoassay for the determination of an anti-parent-antibody antibody in a sample of a human being. Preferably said conjugate is added in this embodiment to the sample of a human being prior to the immunoassay.

The parent antibody is preferably a therapeutic antibody. Also preferably the parent antibody is a murine antibody, chimeric antibody, humanized antibody, or human antibody. Preferably the parent antibody is a chimeric antibody, humanized antibody, or human antibody. Especially preferred is said parent antibody a therapeutic chimeric, humanized, or human antibody. For the detection of antibodies against a parent antibody different methods can be employed, such as radioimmunoassay (RIA), enzyme linked immunosorbent assay (ELISA), immunoradiometric assays (IRMA), or surface plasmon resonance (SPR).

The term "therapeutic antibody" and grammatical equivalents thereof used within this application denotes an, preferably monoclonal, antibody which is intended to be administered to mammals, preferably humans, for use in treatment, therapy, or diagnosis of a disease. A therapeutic antibody is generally produced by recombinant means, e.g. by the cultivation of a eukaryotic cell transfected with a nucleic acid encoding said therapeutic antibody. Preferably the therapeutic antibody is a chimeric antibody, or a humanized antibody, or a human antibody. The therapeutic antibody is administered to achieve a desired effect, such as e.g. depletion of target cells, or mediation of ADCC (antibody-dependent cell-mediated cytotoxicity), or mediation of CDC (complement dependent cytotoxicity). Target cells may be e.g. cancer cells, or virus-infected cells. To mediate ADCC or CDC the therapeutic antibody has to bind to the target cell and is thus specific for, i.e. specifically binding, e.g. a tumor antigen.

A "tumor antigen," as used herein, includes the meaning known in the art, which includes any molecule expressed on (or associated with the development of) a tumor cell that is known or thought to contribute to a tumorigenic characteristic of the tumor cell. Numerous tumor antigens are known in the art. Whether a molecule is a tumor antigen can also be determined according to techniques and assays well known to those skilled in the art, such as for example clonogenic assays, transformation assays, in vitro or in vivo tumor formation assays, gel migration assays, gene knockout analysis, etc. Preferably the term "tumor antigen" when used herein refers to a human transmembrane protein, i.e. a cell membrane protein which is anchored in the lipid bilayer of cells. The human transmembrane protein will generally comprise an "extracellular domain" as used herein, which may bind a ligand, a lipophilic transmembrane domain, a conserved intracellular domain, e.g. a tyrosine kinase domain, and a carboxyl-terminal signaling domain harboring several tyrosine residues which can be phosphorylated. The tumor antigen include molecules such as EGFR, HER2/neu, HER3, HER4, EpCAM, CEA, TRAIL, TRAIL-receptor 1, TRAIL-receptor 2, lymphotoxin-beta receptor, CCR4, CD 19, CD20, CD22, CD28, CD33, CD40, CD80, CSF-1R, CTLA-4, fibroblast activation protein (FAP), hepsin, melanoma-associated chondroitin sulfate proteoglycan (MCSP), prostate-specific membrane antigen (PSMA), VEGF receptor 1, VEGF receptor 2, IGF1-R, TSLP-R, TIE-1, TIE-2, TNF-alpha, TNF like weak inducer of apoptosis (TWEAK), or IL-1R.

Preferably the conjugate according to the invention is used as a standard in an immunological determination of an anti-parent-antibody antibody in a sample, using a sandwich immunoassay comprising a capture antibody and a tracer antibody. Especially preferred said capture or said tracer antibody is said parent antibody.

For example, anti-drug antibody assays are mentioned in WO 2005/045058, and WO 90/006515, anti-idiotypic antibody assays are mentioned in U.S. Pat. No. 5,219,730, WO 87/002778, EP 0 139 389, and EP 0 170 302.

Preferably said anti-idiotype antibody is a monoclonal antibody and said reference immunoglobulin is a polyclonal human immunoglobulin. Also preferably said anti-idiotype antibody is a monoclonal antibody and said reference immunoglobulin is a monoclonal human immunoglobulin.

The conjugate according to the invention is preferably used as a standard in an immunological determination of an anti-idiotype antibody against a parent antibody in a sample. For the immunological determination a capture and a tracer antibody are employed. In one embodiment the capture antibody is the parent antibody. Preferably the parent antibody used as the capture antibody is a complete antibody, i.e. it comprises a light and a heavy chain whereby the light chain comprises a variable domain and a constant domain, and whereby the heavy chain comprises a variable domain, a $C_H1$, a $C_H2$, a $C_H3$, and an optional $C_H4$ domain and a hinge region. Preferably the capture antibody is selected from the group comprising the light chain, the variable region of the heavy chain, a Fab, Fab', F(ab)$_2$, or F(ab')$_2$ fragment of said parent antibody, i.e. it is either the light chain, the variable region of the heavy chain, the Fab, or Fab', or F(ab)$_2$, or F(ab')$_2$ fragment of said parent antibody. In an other embodiment the tracer antibody is the parent antibody. In this embodiment e.g. the conjugate according to the invention is bound via an immunoglobulin specifically binding the reference immunoglobulin of the conjugate to the solid support.

The conjugation of a tracer and/or capture antibody to its conjugation partner can be performed by different methods, such as passive adsorption, chemical binding, or binding via a specific binding pair. The term "conjugation partner" as used herein denotes e.g. solid supports, polypeptides, detectable labels, members of specific binding pairs. In one embodiment the conjugation of the capture and/or tracer antibody to its conjugation partner is performed by chemically binding via N-terminal and/or ε-amino groups (lysine), ε-amino groups of different lysines, carboxy-, sulfhydryl-, hydroxyl-, and/or phenolic functional groups of the amino acid backbone of the antibody, and/or sugar alcohol groups of the carbohydrate structure of the antibody. In one embodiment the capture and/or tracer antibody are/is conjugated to its conjugation partner via a specific binding pair. Preferably the capture antibody is conjugated to biotin and immobilization to a solid support is performed via solid support immobilized avidin or streptavidin. Preferably the tracer antibody is conjugated to digoxigenin and linking to the detectable label is performed via an antibody against digoxigenin. The capture antibody is in another embodiment conjugated to the solid support by passive adsorption. An antibody conjugated to the solid support by passive adsorption comprises a mixture of antibodies conjugated to the solid support via different antibody sites. Thus, the capture antibody conjugated to the solid support by passive adsorption is a mixture of two or more different conjugates wherein the conjugates differ in the antibody sites, i.e. the antibody residues, with which the conjugation to the solid support is effected. Passive adsorption is, e.g., described by Butler, J. E., in "Solid Phases in Immunoassay", page 205-225; Diamandis, E. P. and Christopoulos, T. K. (Editors): Immunoassays (1996), Academic Press, San Diego.

In a preferred embodiment of the invention, the capture antibody is immobilized via a specific binding pair. Such a binding pair (first component/second component) is, for example, streptavidin or avidin/biotin, antibody/antigen (see, for example, Hermanson, G. T., et al., Bioconjugate Techniques, Academic Press, 1996), lectin/polysaccharide, steroid/steroid binding protein, hormone/hormone receptor, enzyme/substrate, IgG/Protein A and/or G and/or L, etc. Preferably, the capture parent antibody is conjugated to biotin and immobilization is performed via immobilized avidin or streptavidin. In an other preferred embodiment of the invention, the tracer antibody is conjugated to a detectable label, preferably conjugated via a specific binding pair. Such a binding pair (first component/second component) is, for example, Streptavidin or Avidin/biotin, antibody/antigen, lectin/polysaccharide, steroid/steroid binding protein, hormone/hormone receptor, enzyme/substrate, IgG/Protein A and/or G and/or L, etc. Preferably, the tracer parent antibody is conjugated via digoxigenin and an antibody against digoxigenin to the detectable label. Alternatively the tracer parent antibody is conjugated to an electrochemiluminescent label, like a ruthenium bispyridyl complex.

If the conjugate according to the invention is used as a standard in an immunoassay for the determination of an anti-idiotype antibody against a parent antibody in a sample of a human being it is preferably used in two or more different concentrations. With the determined responses to the different concentrations of the standard a calibration curve is/can be calculated.

If the conjugate according to the invention is used as a standard in an immunoassay for the determination of an anti-idiotype antibody against a parent antibody in a sample of a human being an (optional) additional antibody specifically binding said reference immunoglobulin of said conjugate can be employed. The conjugate according to the invention can be used as a standard alone or in combination with the optional additional anti-human-immunoglobulin antibody (FIGS. 3 and 4).

The term "standard" or "standard substance" which can be used interchangeably within this application denotes a point of reference for an analytical method and is used to set up a value against which other results of the same analytical method are compared. The term "positive control" as used herein denotes a standard substance with which, if employed in an analytical method, a response above a defined cut-off or threshold value will be achieved. The cut off value is in general the average value obtained in the analysis of samples not containing anti-drug antibodies plus two times, preferably three times, the standard deviation of the obtained values.

The invention further comprises a method for the use of a conjugate according to the invention as a standard in an immunoassay comprising the following steps a) contacting the conjugate according to the invention with a capture antibody, b) detecting the binding of said conjugate to said capture antibody. The detection of the binding in step a) can be performed either directly, e.g. via a change in the SPR angel, or indirectly, e.g. via a tracer antibody and/or a detectable label.

The invention further comprises a method for the determination whether an anti-drug antibody is binding to the Fc-region or the Fab-region of a parent antibody and which immunoglobulin class said anti-drug antibody has (see e.g. FIG. 7). In this method the binding of a sample is determined with immobilized parent antibody, immobilized Fc-region of said parent antibody, and/or immobilized Fab-region of said parent antibody. This can be performed e.g. on a BIAcore chip, on which one of the four channels contains the immobilized parent antibody, one contains the immobilized Fc-region of the parent antibody, one contains the immobilized Fab-region of the parent antibody, and one contains no immobilized parent antibody. Depending on which channels and therefore which part(s) of the parent antibody show binding of an anti-drug antibody from the sample the binding region of an anti-drug antibody can be determined. The immunoglobulin class is determined by binding of anti-human-immunoglobulin-E antibody, anti-human-immunoglobulin-M antibody, anti-human-immunoglobulin-G antibody, or anti-human-immunoglobulin-A antibody. The anti-human-immunoglobulin antibodies are either used sequentially or concomitantly, preferably sequentially. The conjugate according to the invention can be used as a standard in this method.

The invention further comprises a method for the determination of the immunoglobulin class of an anti-idiotype antibody specifically binding a CDR region of a parent antibody in a sample using a sandwich immunoassay comprising a capture antibody, a tracer antibody, and a conjugate according to the invention, comprising the following steps:

a) contacting said sample with the capture antibody under conditions suitable for the formation of a capture antibody/anti-idiotype antibody-complex,
b) contacting separately
  i) an anti-human-immunoglobulin-A antibody,
  ii) an anti-human-immunoglobulin-E antibody,
  iii) an anti-human-immunoglobulin-M antibody, and
  iv) an anti-human-immunoglobulin-G antibody
as tracer antibodies with said capture antibody/anti-idiotype antibody-complex,
c) determining the binding of each of said tracer antibodies to said complex and thereby determining the immunoglobulin class of said anti-idiotype antibody,
wherein a conjugate according to the invention is used as a positive control.

A scheme of this method and an exemplary response diagram are given in FIGS. 1 and 2.

Preferably said tracer antibodies are contacted in the order i) anti-human-immunoglobulin-A antibody, ii) anti-human-immunoglobulin-E antibody, iii) anti-human-immunoglobulin-M antibody, and iv) anti-human-immunoglobulin-G antibody with said capture antibody/anti-idiotype antibody-complex, i.e. the tracer antibodies are contacted sequentially.

Preferably said capture antibody is selected from the group comprising the light chain, the variable region of the heavy chain, a Fab, Fab', F(ab)$_2$, or F(ab')$_2$ fragment of said parent antibody.

The invention further comprises a polyclonal antibody specifically binding a CDR region of an anti-IL-6R antibody. A method for the preparation of a polyclonal antibody according to the invention is described in Example 1a).

Preferably the method for the determination of the immunoglobulin class of an anti-idiotype antibody according to the invention comprises the following steps:

a) contacting said sample with the capture antibody under conditions suitable for the formation of a capture antibody/anti-idiotype antibody-complex,
b) contacting a tracer antibody selected from the group of tracer antibodies comprising anti-human-immunoglobulin-G antibody, anti-human-immunoglobulin-E antibody, anti-human-immunoglobulin-M antibody, anti-human-immunoglobulin-A antibody with said capture antibody/anti-idiotype antibody-complex,
c) determining the binding of said tracer antibody to said complex,
d) disintegrating said capture antibody/anti-idiotype antibody-complex,
e) repeating steps a) to d) with a not previously selected tracer antibody,
f) determining the immunoglobulin class of said anti-idiotypic antibody to be the immunoglobulin of said tracer antibody specifically binding said capture antibody/anti-idiotype antibody-complex.

The tracer antibody is preferably selected from anti-human-immunoglobulin-G antibodies, or anti-human-immunoglobulin-E antibodies, or anti-human-immunoglobulin-M antibodies, or anti-human-immunoglobulin-A antibodies.

The term "under conditions suitable for the formation of a [ . . . ] complex" and grammatical equivalents thereof as used within this application denotes conditions at which an antibody/immunoglobulin of interest, e.g. an anti-idiotype antibody, binds to a second antibody when brought in contact with it. This does not necessarily denote that 100% of the antibody of interest is bound but essentially 100% of the antibody of interest is bound, i.e. at least 85% of the antibody of interest is bound, preferably at least 90% of the antibody of interest is bound, preferably at least 95% of the antibody of interest is bound, more preferably more than 95% of the antibody of interest is bound to the second antibody.

The following examples and figures are provided to aid the understanding of the present invention, the true scope of which is set forth in the appended claims. It is understood that modifications can be made in the procedures set forth without departing from the spirit of the invention.

The use of an antibody against the IL-6 receptor in the following examples is only for exemplifying the invention and does not mean to limit the scope of the invention.

EXAMPLE 1

Preparation of a Composition of a Polyclonal Anti-Idiotype Antibody Specifically Binding to a CDR region of a parent antibody and a polyclonal human serum immunoglobulin of class E, G, A, and M.
Polyclonal Anti-Anti-IL-6R Antibody Antibodies (Anti-Anti-IL-6R-Mab Pab)
i) Preparation of Polyclonal Antibodies Against Monoclonal Anti-IL-6R Antibody
Purification of Polyclonal Antibodies from Rabbit Serum Rabbits have been immunized with monoclonal anti-IL-6R antibody according to standard methods. In the raw serum of five immunized rabbits the lipid components were removed by delipidation with Aerosil (1.5% (w/v)) and the immunoglobulins were precipitated with ammonium sulphate (1.7 M). After acid treatment (30 min., pH 5.5) and dialysis against 15 mM potassium phosphate buffer, supplemented with 50 mM NaCl, pH 7.0, the mixture was separated by DEAE ion exchange chromatography at pH 7.0. The immunoglobulin G fraction was in the flow through (=rabbit anti-anti-IL-6R-mAb pAb) and was concentrated to about 25 mg/ml.
Preparation of Rabbit Anti-Anti-IL-6R-mAb Antibodies Specifically Binding a CDR Region of the Parent Antibody Against IL-6R The concentrated IgG fraction of the previous step was transferred to a buffer system with 50 mM potassium phosphate, supplemented with 150 mM NaCl, pH 7.5 (PBS). The immunosorbent with immobilized anti-IL-6R antibody (parent antibody), prepared by conjugation of anti-IL-6R antibody to NHS-sepharose by state of the art techniques, was packed into a column and equilibrated with 50 mM potassium phosphate buffer, supplemented with 150 mM NaCl, pH 7.5.

10 mg concentrated immunoglobulin G fraction/ml immunosorbent were applied to the column equilibrated with PBS. The column was washed successively with PBS, 0.5 M NaCl supplemented with 0.05% (w/v) Tween® 20, and 30 mM NaCl. The IgG specifically bound to the immunosorbent was eluted with 3 mM HCR and 1 M propionic acid. The eluate was dialyzed against PBS.

To eliminate antibodies with cross reactivity to the human immunoglobulin G (IgG) constant region the affinity-purified antibodies were applied to an affinity column with immobilized human IgG, prepared by conjugation of unspecific human IgG to NHS-sepharose by state of the art techniques. The column was equilibrated with PBS. About 6 mg IgG/ml immunosorbent were applied to the column. The desired specific polyclonal IgG-fraction is in the flow through. After regeneration of the column with 0.5 M NaCl supplemented with 0.05% (w/v) Tween® 20, 30 mM NaCl, 1 M propionic acid, and PBS. The immunosorption of antibodies unspecifically binding to the human IgG constant region was repeated two times to completely eliminate antibodies with cross reactivity against human IgG.

The resulting purified polyclonal anti-anti-IL-6R-antibody antibody without cross reactivity to human IgG constant region was concentrated to about 4 mg/ml and stored at −80° C.
ii) Conjugation of the Polyclonal Anti-Anti-IL-6R-Antibody Antibody to Polyclonal Human Immunoglobulin E, Human Immunoglobulin G, Human Immunoglobulin A, and Human Immunoglobulin M
Preparation of a Conjugate of Polyclonal Rabbit Anti-Anti-IL-6R-Antibody Antibody (aa-IL-6R pAb) with Human Immunoglobulin G
Step 1: Preparation of Rabbit aa-IL-6R pAb-SATP The aa-IL-6R pAb was dialyzed against 100 mM potassium phosphate buffer, containing 150 mM NaCl, pH 7.8, and the protein solution was adjusted to a protein concentration of about 15 mg/ml. N-succinimidyl-3-acetylthiopropionate (SATP) was dissolved in DMSO and added to the antibody solution in a molar ratio of 1:5 (aa-IL-6R pAb:SATP). The pH was adjusted to pH 7.1 and the mixture was incubated for 60 min. at 25° C. The reaction was stopped by adding L-lysine at a final concentration of 10 mM and the surplus of SATP was removed by dialysis against 10 mM potassium phosphate buffer, containing 200 mM NaCl, 1 mM EDTA, pH 6.1.
Step 2: Preparation of human polyclonal human immunoglobulin G-MH The polyclonal human antibody was dialyzed against 30 mM potassium phosphate buffer, pH 7.4, and the protein solution was thereafter adjusted to a protein concentration of about 25 mg/ml. Maleimidohexanoyl-N-hydroxysuccinimide ester (MHS) was dissolved in DMSO and added to the antibody solution in a molar ratio of 1:6 (IgG:MHS). The pH was adjusted to pH 7.1 and the mixture was incubated 60 min at 25° C. The reaction was stopped by adding L-lysine to a final concentration of 10 mM, the pH was adjusted to pH 6.2, and the surplus of MHS was removed by dialysis against 10 mM potassium phosphate buffer, containing 200 mM NaCl, 1 mM EDTA, pH 6.1.
Step 3: Conjugation of aa-IL-6R pAb-SATP with polyclonal human immunoglobulin G-MH aa-IL-6R pAb-SATP was deacetylated to aa-IL-6R pAb-SH by incubation with 2% (v/v) 1 M hydroxylamine, pH 7.5, and incubated for 45 min. at 25° C. The deacetylated antibody was mixed with polyclonal human immunoglobulin G-MH (molar ratio of IgG-SH:IgG-MH=1:3) and diluted with 10 mM potassium phosphate buffer, containing 200 mM NaCl, 1 mM EDTA, pH 6.1, to a final concentration of 1.5 mg/ml aa-IL-6R pAb-SH and 4.5 mg/ml polyclonal human immunoglobulin G-MH. The pH was adjusted to pH 7.1 and the mixture was incubated at 25° C. The conjugation process was analyzed with an analytical gel filtration column (e.g. TSK 3000). The conjugation was stopped generally after 45 min. by the addition of cysteine to a final concentration of 1 mM. After a further 30 min. incubation time N-methylmaleimide (NMM) was added to a final concentration of 5 mM and the pH was adjusted to pH 7.5. After 60 min. incubation at 25° C. the conjugate was purified by S300 gel filtration chromatography to eliminate non conjugated antibodies.
Preparation of a Conjugate of Rabbit aa-IL-6R pAb with Human Immunoglobulin M
Step 1: Preparation of Rabbit aa-IL-6R pAb-SATP The aa-IL-6R pAb was dialyzed against 100 mM potassium phosphate buffer, containing 150 mM NaCl, pH 7.8, and the protein solution was adjusted to a protein concentration of about 15 mg/ml. N-succinimidyl-3-acetylthiopropionate (SATP) was dissolved in DMSO and added to the antibody solution in a molar ratio of 1:5 (aa-IL-6R pAb:SATP). The pH was adjusted to pH 7.1 and the mixture was incubated for 60 min. at 25° C. The reaction was stopped by adding L-lysine at a final concentration of 10 mM and the surplus of SATP was removed by dialysis against 10 mM potassium phosphate buffer, containing 200 mM NaCl, 1 mM EDTA, pH 6.1.

Step 2: Preparation of polyclonal human immunoglobulin M-MH

The polyclonal human antibody was dialyzed against 30 mM potassium phosphate buffer, pH 7.4, and the obtained protein solution was adjusted afterwards to a protein concentration of about 20 mg/ml. Maleimidohexanoyl-N-hydroxysuccinimide ester (MHS) was dissolved in DMSO and added to the antibody solution in a molar ratio of 1:50 (IgM:MHS). The pH was adjusted to pH 7.1 and the mixture was incubated for 60 min. at 25° C. The reaction was stopped by adding L-lysine to a final concentration of 10 mM. The pH was adjusted to pH 6.2 and the surplus of MHS was removed by dialysis against 10 mM potassium phosphate buffer, containing 200 mM NaCl, 1 mM EDTA, pH 6.1.

Step 3: Conjugation of aa-IL-6R pAb-SATP with polyclonal human immunoglobulin M-MH aa-IL-6R pAb-SATP was deacetylated to aa-IL-6R pAb-SH by incubation with 2% (v/v) 1 M hydroxylamine, pH 7.5, and incubated for 45 min. at 25° C. The deacetylated antibody was mixed with polyclonal human immunoglobulin M-MH (molar ratio of aa-IL-6R pAb-SH:IgM-MH=1:2) and diluted with 10 mM potassium phosphate buffer, containing 200 mM NaCl, 1 mM EDTA, pH 6.1, to a final concentration of about 0.9 mg/ml aa-IL-6R pAb-SH and 9.1 mg/ml polyclonal human immunoglobulin M-MH. The pH was adjusted to pH 7.1 and the mixture was incubated at 25° C. The conjugation process was monitored with an analytical gel filtration column (e.g. TSK 5000). The conjugation reaction was stopped generally after 60 min. by adding cysteine to a final concentration of 1 mM. After a further 30 min. incubation time N-methylmaleimide (NMM) was added to a final concentration of 5 mM and the pH was adjusted to pH 7.5. After 60 min. incubation at 25° C. the conjugate was purified by S400 gel filtration chromatography to eliminate non conjugated antibodies.

Preparation of a Conjugate of Rabbit aa-IL-6R pAb with Polyclonal Human Immunoglobulin E Step 1: Preparation of Rabbit aa-IL-6R pAb-SATP The aa-IL-6R pAb was dialyzed against 100 mM potassium phosphate buffer, containing 150 mM NaCl, pH 7.8, and the protein solution was adjusted to a protein concentration of about 15 mg/ml. N-succinimidyl-3-acetylthiopropionate (SATP) was dissolved in DMSO and added to the antibody solution in a molar ratio of 1:5 (aa-IL-6R pAb:SATP). The pH was adjusted to pH 7.1 and the mixture was incubated for 60 min. at 25° C. The reaction was stopped by adding L-lysine at a final concentration of 10 mM and the surplus of SATP was removed by dialysis against 10 mM potassium phosphate buffer, containing 200 mM NaCl, 1 mM EDTA, pH 6.1.

Step 2: Preparation of Polyclonal Human Immunoglobulin E-MH

The polyclonal human antibody was dialyzed against 30 mM potassium phosphate buffer, pH 7.4, and the obtained protein solution was adjusted to a final protein concentration of about 13 mg/ml. Maleimidohexanoyl-N-hydroxysuccinimide ester (MHS) was dissolved in DMSO and added to the antibody solution in a molar ratio of 1:6 (IgE:MHS). The pH was adjusted to pH 7.1 and the mixture was incubated for 60 min. at 25° C. The reaction was stopped by adding L-lysine to a final concentration of 10 mM, the pH was adjusted to pH 6.2 and surplus of MHS was removed by dialysis against 10 mM potassium phosphate buffer, containing 200 mM NaCl, 1 mM EDTA, pH 6.1.

Step 3: Conjugation of Rabbit aa-IL-6R pAb-SATP with Polyclonal Human Immunoglobulin E-MH aa-IL-6R pAb-SATP was deacetylated to aa-IL-6R pAb-SH by incubation with 2% (v/v) 1 M hydroxylamine, pH 7.5, and incubated for 45 min. at 25° C. The deacetylated antibody was mixed with polyclonal human immunoglobulin E-MH (molar ratio of aa-IL-6R pAb-SH:IgE-MH=1:1.7) and diluted with 10 mM potassium phosphate buffer, containing 200 mM NaCl, 1 mM EDTA, pH 6.1, to a concentration of 2.9 mg/ml aa-IL-6R pAb-SH and 6.3 mg/ml polyclonal human immunoglobulin E-MH. The pH was adjusted to 7.1 and the mixture was incubated at 25° C. The conjugation process was monitored with an analytical gel filtration column (e.g. TSK 4000). The conjugation process was stopped generally after 90 min. by adding cysteine to a final concentration of 1 mM. After a further 30 min. incubation time N-methylmaleimide (NMM) was added to a final concentration of 5 mM and the pH was adjusted to pH 7.5. After 60 min. incubation at 25° C. the conjugate was purified by S300 gel filtration chromatography to eliminate non conjugated antibodies.

Preparation of a Conjugate of Rabbit Aa-IL-6R pAb with Polyclonal Human Immunoglobulin A Step 1: Preparation of Rabbit aa-IL-6R pAb-SATP The aa-IL-6R pAb was dialyzed against 100 mM potassium phosphate buffer, containing 150 mM NaCl, pH 7.8, and the protein solution was adjusted to a protein concentration of about 15 mg/ml. N-succinimidyl-3-acetylthiopropionate (SATP) was dissolved in DMSO and added to the antibody solution in a molar ratio of 1:5 (aa-IL-6R pAb:SATP). The pH was adjusted to pH 7.1 and the mixture was incubated for 60 min. at 25° C. The reaction was stopped by adding L-lysine at a final concentration of 10 mM and the surplus of SATP was removed by dialysis against 10 mM potassium phosphate buffer, containing 200 mM NaCl, 1 mM EDTA, pH 6.1.

Step 2: Preparation of polyclonal human immunoglobulin A-MH

The polyclonal human antibody is dialyzed against 30 mM potassium phosphate buffer, pH 7.4, and the obtained protein solution is adjusted to a final protein concentration of about 13 mg/ml. Maleimidohexanoyl-N-hydroxysuccinimide ester (MHS) is dissolved in DMSO and added to the antibody solution in a molar ratio of 1:6 (IgA:MHS). The pH is adjusted to pH 7.1 and the mixture is incubated for 60 min. at 25° C. The reaction is stopped by adding L-lysine to a final concentration of 10 mM, the pH is adjusted to pH 6.2 and surplus of MHS is removed by dialysis against 10 mM potassium phosphate buffer, containing 200 mM NaCl, 1 mM EDTA, pH 6.1.

Step 3: Conjugation of rabbit aa-IL-6R pAb-SATP with polyclonal human immunoglobulin A-MH aa-IL-6R pAb-SATP was deacetylated to aa-IL-6R pAb-SH by incubation with 2% (v/v) 1 M hydroxylamine, pH 7.5, and incubated for 45 min. at 25° C. The deacetylated antibody is mixed with polyclonal human immunoglobulin A-MH (molar ratio of aa-IL-6R pAb-SH:IgA-MH=1:2) and diluted with 10 mM potassium phosphate buffer, containing 200 mM NaCl, 1 mM EDTA, pH 6.1, to a concentration of 2.9 mg/ml aa-IL-6R pAb-SH and 6.3 mg/ml polyclonal human immunoglobulin A-MH. The pH is adjusted to 7.1 and the mixture is incubated at 25° C. The conjugation process is monitored with an analytical gel filtration column (e.g. TSK 4000). The conjugation process is stopped generally after 90 min. by adding cysteine to a final concentration of 1 mM. After a further 30 min. incubation time N-methylmaleimide (NMM) is added to a final concentration of 5 mM and the pH is adjusted to pH 7.5. After 60 min. incubation at 25° C. the conjugate is purified by S300 gel filtration chromatography to eliminate non conjugated antibodies.

EXAMPLE 2

Coupling of Biotinylated Anti-IL-6R Antibodies to a Streptavidin Coated Chip The anti-IL-6R antibody has been dialyzed against buffer (100 mM potassium phosphate buffer, pH 8.5). Afterwards the solution was adjusted to a protein concentration of 10 mg/ml. D-biotinoyl-aminocaproic acid-N-hydroxysuccinimide ester was dissolved in DMSO and added to the antibody solution in a molar ratio of 1:5. After 60 minutes the reaction was stopped by adding L-lysine. The surplus of the labeling reagent was removed by dialysis against 25 mM potassium phosphate buffer supplemented with 150 mM sodium chloride, pH 7.5.

The surface of a flow cell of a CM5 chip was activated with a NHS-EDC mixture in the first step. After surface activation, a 100 µg/ml solution of Neutravidin (diluted in buffer with pH 4.5; Pierce) was injected to allow for the formation of covalent bonds to the activated surface esters. Afterwards inactivation of residual uncoupled esters was achieved through injection of 1 M ethanolamine. Biotinylated antibody was injected over a single flow cell with a flow of 20 µl/min and a concentration of 20 µg/ml for 5 minutes. This led to the immobilization of the antibody to the flow cell.

EXAMPLE 3

Detection of IgG Class Anti-Anti-IL-6R-Antibody Antibodies in Human Serum

The sample was diluted between 1:10 to 1:100 and injected in 20 µl volumes at a flow rate of 20 µl/min on a chip as prepared in Example 2. After sample injection, the anti IgG-class antibody mAb anti-human-immunoglobulin-G antibody was injected at a flow rate of 20 µl/min and a concentration of 20 µg/ml. Finally, one injection of regeneration solution (100 mM $H_3PO_4$) was performed. A standard sample was measured at the start of each measurement. 20 µl of a conjugate of polyclonal rabbit anti-anti-IL-6R-antibody antibody (aa-IL-6R pAb) with human IgG as positive standard was injected over an immunogenicity chip, with an immobilized complete antibody, F(ab')$_2$-fragment, and/or Fc fragment of anti-IL-6R antibody at a flow rate of 20 µl/min. After standard injection, optionally the anti Ig-class antibody mAb anti-human-immunoglobulin G antibody was injected at the same flow rate.

EXAMPLE 4

Detection of IgE Class Anti-Anti-IL-6R-Antibody Antibodies in Human Serum

The sample was diluted between 1:10 to 1:100 and injected in 20 µl volumes at a flow rate of 20 µl/min on a chip as prepared in Example 2. After sample injection, the anti IgE-class antibody mAb anti-human-immunoglobulin E antibody was injected at a flow rate of 20 µl/min and a concentration of 20 µg/ml. Finally, one injection of regeneration solution (100 mM $H_3PO_4$) was performed. A standard sample was measured at the start of each measurement. 20 µl of a conjugate of rabbit aa-IL-6R pAb with human IgE as positive standard was injected over an immunogenicity chip, with an immobilized complete antibody, F(ab')$_2$-fragment, and/or Fc fragment of anti-IL-6R antibody at a flow rate of 20 µl/min. After standard injection, optionally the anti IgE-class antibody mAb anti-human-immunoglobulin E antibody was injected at the same flow rate.

EXAMPLE 5

Detection of IgM Class Anti-Anti-IL-6R-Antibody Antibodies in Human Serum

The sample was diluted between 1:10 to 1:100 and injected in 20 µl volumes at a flow rate of 20 µl/min on a chip as prepared in Example 2. After sample injection, the anti IgM-class antibody mAb anti-human immunoglobulin M was injected at a flow rate of 20 l/min and a concentration of 20 µg/ml. Finally, one injection of regeneration solution (100 mM $H_3PO_4$) was performed. A standard sample was measured at the start of each measurement. 20 µl of a conjugate of rabbit aa-IL-6R pAb with human IgM as positive standard was injected over an immunogenicity chip, with an immobilized complete antibody, F(ab')$_2$-fragment, and/or Fc fragment of anti-IL-6R antibody at a flow rate of 20 µl/min. After standard injection, optionally the anti IgM-class antibody mAb anti-human-immunoglobulin M antibody was injected at the same flow rate.

EXAMPLE 6

Detection of IgE, IgG, and IgM Class Anti-Anti-IL-6R-Antibody Antibodies in Human Serum The sample was diluted between 1:10 to 1:100 and injected in 20 µl volumes at a flow rate of 20 µl/min on a chip as prepared in Example 2. After sample injection, the anti IgE-class antibody mAb anti-human-immunoglobulin E was injected at a flow rate of 20 µl/min and a concentration of 20 µg/ml. After the injection the response was recorded. Afterwards the anti IgM-class antibody mAb anti-human-immunoglobulin M was injected at a flow rate of 20 µl/min and a concentration of 20 µg/ml. After the injection the response was recorded. Afterwards the anti IgG-class antibody mAb anti-human-immunoglobulin G was injected at a flow rate of 20 µl/min and a concentration of 20 µg/ml. After the injection the response was recorded. Finally, one injection of regeneration solution (100 mM $H_3PO_4$) was performed. The three described standard samples (conjugates) were measured at the start of each measurement. Standard 1: 20 µl of a conjugate of rabbit aa-IL-6R pAb with human IgM as positive standard was injected over an immunogenicity chip; Standard 2: 20 µl of a conjugate of rabbit aa-IL-6R pAb with human IgE as positive standard was injected over an immunogenicity chip; Standard 3: 20 µl of a conjugate of rabbit aa-IL-6R pAb with human IgG as positive standard was injected over an immunogenicity chip.

EXAMPLE 7

ELISA-Determination of Anti-Parent Antibodies of the IgE Class Using a Standard Conjugate In the first step biotinylated antibody against the IL-6 receptor (parent antibody) was bound on the surface in the wells of a Streptavidin-coated microtiterplate (SA-MTP). Unbound antibody was removed by washing with universal buffer. Afterwards the samples and the reference standards (rabbit antibody against anti-IL-6 receptor antibody conjugated to polyclonal human IgE) were added to different wells and incubated. Anti-parent antibody from the sample and the reference standard, respectively, binds to the immobilized parent antibody. After a washing step the bound anti-parent antibody and the reference standard, respectively, were detected with digoxigenylated antibody against human IgE followed by incubation with a horseradish peroxidase labeled anti-digoxigenin-antibody. The antibody-enzyme conjugate catalyzes the color reaction of ABTS® substrate. The signal is measured by ELISA reader at 405 nm wavelength (reference wavelength: 490 nm). Absorbance values of each serum sample are determined in triplicates. A positive signal was obtained for the standard and also for the sample in case the anti-parent antibody is of the IgE subclass (FIGS. 5 and 6).

The invention claimed is:

1. A conjugate for use in an immunoassay comprising a complete anti-idiotype antibody and a reference immunoglobulin, wherein said anti-idiotype antibody
   a) is chemically bonded to said reference immunoglobulin via a non-peptide bond, and
   b) binds to a complementarity determining region (CDR) of a monoclonal therapeutic antibody, wherein the therapeutic antibody is a monoclonal antibody intended to be administered to mammals for use in treatment, therapy or diagnosis of a disease; and
   wherein said reference immunoglobulin is of a single immunoglobulin class and comprises a complete human immunoglobulin or a human immunoglobulin Fc-region.

2. The conjugate of claim 1, wherein said reference immunoglobulin is not specifically binding said anti-idiotype antibody and not specifically binding said therapeutic antibody.

3. The conjugate of claim 2, wherein the reference immunoglobulin is a complete human immunoglobulin.

4. The conjugate of claim 2, wherein the reference immunoglobulin is selected from the group consisting of IgE, IgM and IgA.

5. A method for determining an anti-therapeutic-antibody antibody in a sample in a sandwich immunoassay and with the conjugate of claim 1 as a standard or positive control, wherein said immunoassay comprises as a capture antibody, or as a tracer antibody, the therapeutic antibody or an antigen binding fragment thereof and wherein if the capture antibody or tracer antibody is the therapeutic antibody, then the other respective antibody is an anti-human immunoglobulin antibody or an antigen binding fragment thereof and wherein said anti-therapeutic-antibody antibody is an anti-idiotype antibody against said therapeutic antibody comprising the steps of
   a) determining binding of an anti-idiotype antibody in a sample by
      i) contacting said sample suspected of containing the anti-idiotype antibody with said capture antibody under conditions suitable for forming a capture antibody/anti-idiotype antibody-complex, wherein at least 85% of said anti-idiotype antibody is bound to the capture antibody,
      ii) contacting said tracer antibody with said capture antibody/anti-idiotype antibody-complex of step i) to bind said tracer antibody to the complex, and
      iii) determining the binding of said tracer antibody to said complex of step i),
   b) determining binding of said standard or positive control by
      i) contacting the conjugate of claim 1 with said capture antibody under conditions suitable for forming a capture antibody/standard or positive control-complex,
      ii) contacting said tracer antibody with said capture antibody/standard or positive control-complex of step b)i) to bind said tracer antibody to the complex, and
      iii) determining the binding of said tracer antibody to said complex of step b)i), and
   c) comparing the binding of said tracer antibody to the anti-idiotype antibody from the sample as determined in step a)iii) to the binding of said tracer antibody to the conjugate of claim 1 as determined in step b)iii), and thereby determining presence or amount of said anti-idiotype antibody, and thus determining said anti-therapeutic-antibody antibody in the sample.

6. The method of claim 5, wherein said capture antibody is selected from the group consisting of a light chain, a variable region of a heavy chain, a Fab, Fab', F(ab)2, and F(ab')2 fragment of said therapeutic antibody.

7. A method for determination of the immunoglobulin class of an anti-idiotype antibody binding a complementarity determining region (CDR) of a therapeutic antibody in a sample with a sandwich immunoassay, comprising a capture antibody and a tracer antibody, and the conjugate of claim 1 as a positive control, comprising the following steps:
   a) contacting the sample with the therapeutic antibody or an antigen binding fragment thereof as the capture antibody under conditions suitable for forming a capture antibody/anti-idiotype antibody-complex, wherein at least 85% of the anti-idiotype antibody is bound to the capture antibody
   b) contacting separately different aliquots of the sample obtained in a) containing said capture antibody/anti-idiotype antibody complex with
      i) an anti-human-immunoglobulin-A tracer antibody,
      ii) an anti-human-immunoglobulin-E tracer antibody,
      iii) an anti-human-immunoglobulin-M tracer antibody,
      iv) an anti-human-immunoglobulin-G tracer antibody,
      to form a complex of said tracer antibody with said capture antibody/anti-idiotype antibody complex
   c) contacting the conjugate of claim 1 as a positive control with the capture antibody under conditions suitable for forming a capture antibody/conjugate complex,
   d) contacting separately different aliquots of said capture antibody/anti-idiotype antibody complex in step c) with
      i) an anti-human-immunoglobulin-A tracer antibody,
      ii) an anti-human-immunoglobulin-E tracer antibody,
      iii) an anti-human-immunoglobulin-M tracer antibody,
      iv) an anti-human-immunoglobulin-G tracer antibody,
      to form a complex of said tracer antibody with said capture antibody/anti-idiotype antibody complex, and
   e) determining the binding of said tracer antibodies to the complex as per step b) as compared to the binding of said tracer antibodies to the conjugate of claim 1 as per step d), and thereby determining the immunoglobulin class of said anti-idiotype antibody.

8. The method of claim 7 whereby determining the immunoglobulin class of said anti-idiotype antibody of step e) is by surface plasmon resonance.

* * * * *